Jan. 30, 1962 R. L. BROWN Plant Pat. 2,124
PEACH TREE
Filed March 6, 1961
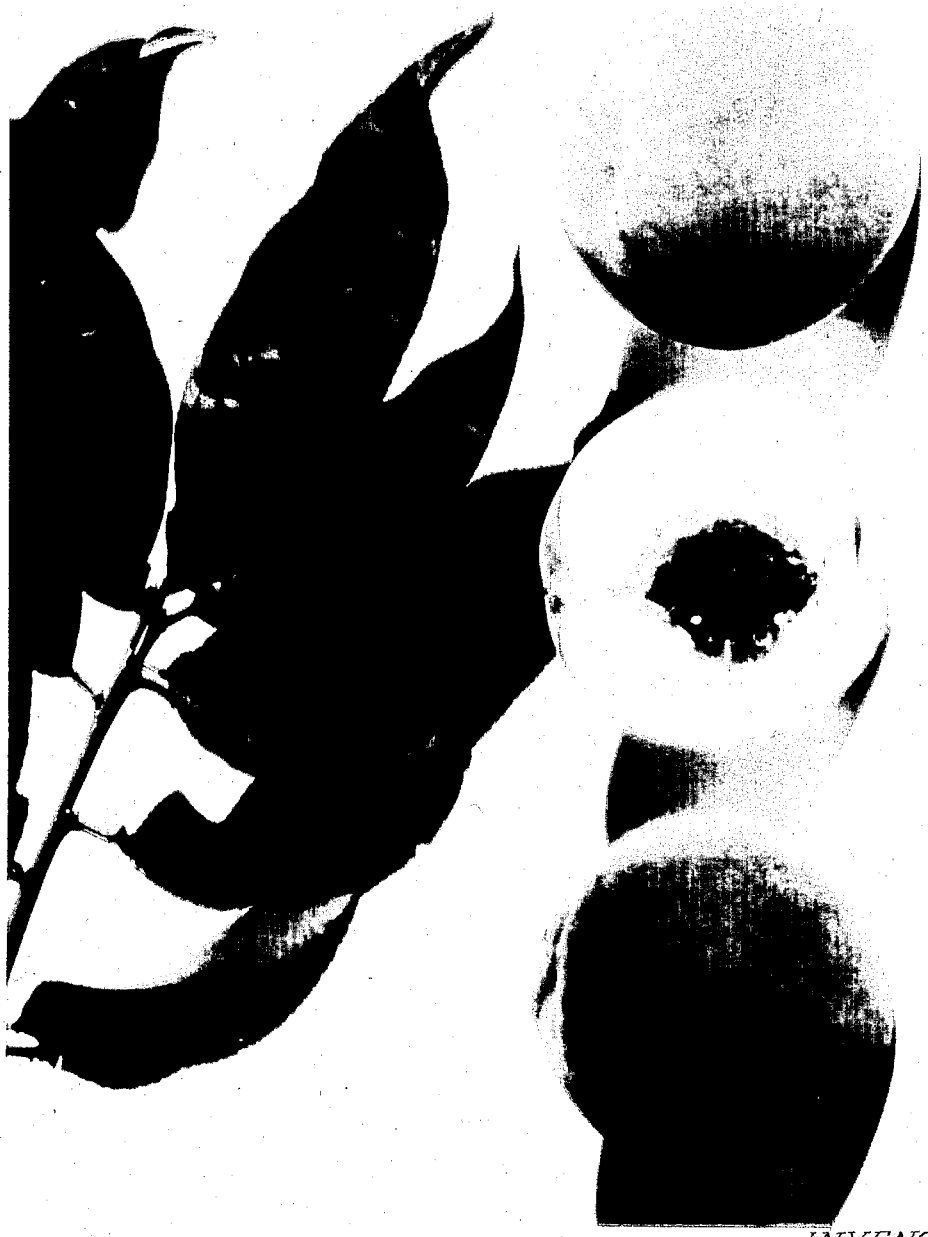
INVENTOR
Robert L. Brown
BY Robb & Robb
ATTORNEYS United States Patent Office Plant Pat. 2,124
Patented Jan. 30, 1962

2,124
PEACH TREE

Robert L. Brown, New Park, Pa., assignor to Stark Bro's Nurseries & Orchards Company, Louisiana, Mo., a corporation of Missouri Filed Mar. 6, 1961, Ser. No. 93,823
1 Claim. (Cl. 47—62)

The present invention relates to a new and distinct variety of peach tree which was discovered by me as a bud sport of the variety known as "Elberta" (unpatented), the discovery having been made by me in my cultivated orchard located in Fawn Township, York County, Pennsylvania, near the village of Gatcheville.

At the time of my discovery aforesaid, I was growing fruit trees on my orchard property, and while picking fruit from an "Elberta" peach tree, my attention was attracted to certain fruit on the tree which appeared to be materially different from the normal fruit of the "Elberta" variety. On closer examination, I found that the tree had sported, and I thereupon took steps to carefully preserve the sport, keep it under close observation, and later to asexually reproduce the same. These continued observations and subsequent tests of both the original sport and the asexual reproductions thereof fully confirmed and established that the sport was definitely different from its parent variety, as well as from all other varieties of which I am aware, as evidenced by the following unique combination of outstanding characteristics which I am convinced represent a new and distinct variety:

(1) General resemblance of the fruit in size, shape and texture to that of the variety "J. H. Hale" (unpatented);

(2) Firm fruit of exceptionally good quality;

(3) High coloration of the fruit which develops a week or 10 days before the fruit ripens;

(4) A habit of ripening about 2 to 3 weeks later than "Elberta," and about 10 days later than "J. H. Hale"; and (5) A distinctly better fruit flavor than that of the fruit of "J. H. Hale."

Asexual reproduction of my new variety by budding, as performed by me in my orchard aforesaid, shows that the foregoing characteristics and distinctions come true to form and are established and transmissible through succeeding propagations.

The accompanying drawing shows typical specimens of the fruit and foliage of my new variety as depicted in color as nearly true as it is reasonably possible to make the same in a color illustration of this character, said fruit specimens being shown in elevation, as well as in cross section.

The following is a detailed description of my new variety, with color terminology in accordance with Ridgway's Color Standards and Nomenclature (hereinafter abbreviated as "Ridgway"), Munsell Color Chart (hereinafter abbreviated as "Munsell") and the Horticultural Colour Guide (hereinafter abbreviated as "HCG"), as indicated, except where general color terms of ordinary dictionary significance are obvious, and based upon observations made from specimens grown in Pike County, Illinois:

Dates of first and last pickings: About September 5 and September 14, respectively.

Tree: Medium large; vigorous; open; spreading; vase-formed; hardy; productive; regular bearer.

*Trunk.*—Medium stockiness; medium smoothness.

*Branches.*—Medium stockiness; smooth. Color—Liver Brown, Plate XIV, color No. 7′, tone M (Ridgway).

*Twigs.* — Color — Dark Vinaceous-Purple, Plate XXXVIII, color No. 67″, tone A (Ridgway).

*Leaves.*—Medium large (about 6 inches long and about 1⅞ inches wide); ovate; acutely pointed; medium thickness; smooth. Margin—glandular; crenate. Color—Parsley Green, Plate 00962, page 193, vol. 2 (HCG). Petiole—medium short; medium thickness. Glands—3 or 4 in number; alternate; medium small; reniform; free; glabrous.

Flowers: Medium late in comparison with other varieties; small size.

*Date of first bloom.*—About April 10.

*Date of full bloom.*—About April 20.

*Color.*—White, with slight pink tinge corresponding to Pale Pink, Plate 2.5R 9/1 (Munsell).

Fruit:

*Maturity when described.*—Eating-ripe (about September 14).

*Size.*—Rather uniform; large. Axial diameter—3 inches. Transverse diameter in suture plane—3 inches. Diameter at right angles to suture plane—2¾ inches.

*Form.*—Uniform; unsymmetrical; broadly ovoid; compressed transversely toward suture.

*Suture.*—Distinct; shallow; extends from base to apex; has slight marked depression beyond pistil point.

*Ventral surface.*—Rounded; strongly lipped toward base; lips equal.

*Cavity.*—Abrupt; circular; suture showing on one side. Depth—9/16 inch. Breadth—¾ inch.

*Base.*—Cuneate.

*Apex.*—Rounded.

*Pistil point.*—Apical.

*Stem.*—Medium stoutness; about ⅜ inch long; medium strong adherence to stone.

*Skin.*—Medium thinness; medium toughness; tenacious to flesh; no tendency to break in wet or dry seasons. Color—highly blushed with Oxblood Red, Plate 00823, page 191, vol. 2 (HCG).

*Flesh.*—Color—Aureolin, Plate 3/2, page 3, vol. 1 (HCG). Surface of pit cavity—Color—Rose Opal, Plate 022/3, page 110, vol. 2, (HCG). Amygadalin—wanting. Juice—moderate quantity; rich. Texture—firm. Fibres—few; fine; tender. Ripens—fairly evenly. Flavor—mild; vinous. Aroma—distinct. Eating quality—best.

*Stone.* — Free. Fibres — long; parts from flesh smoothly. Size — medium large; length — 1½ inches; thickness—¾ inch. Form—obovoid; full toward apex. Base—oblique; hilum narrow oval. Apex—acute. Sides—equal. Surface—irregularly furrowed near base; pitted throughout. Ridges—rounded toward apex. Pits—elongated; wing at center. Dorsal edge—narrow; with deep narrow groove throughout; interrupted.

Use: Market; dessert.

Keeping quality: Good.

Shipping quality: Good.

I claim:

A new and distinct variety of peach tree of the freestone yellow-fleshed fruit type, substantially as herein shown and described, characterized particularly as to novelty by the unique combination of fruit size, shape and texture generally resembling that of the variety "J. H. Hale" (unpatented), firm fruit of exceptionally good quality, high coloration of the fruit which develops from a week to 10 days before the fruit ripens, a habit of ripening from 2 to 3 weeks later than the variety "Elberta" (unpatented) and about 10 days later than "J. H. Hale," and a better fruit flavor than that of the fruit of "J. H. Hale."

No references cited.